(12) United States Patent
Mori et al.

(10) Patent No.: US 10,520,450 B2
(45) Date of Patent: Dec. 31, 2019

(54) SUBSTRATE INSPECTION METHOD, SUBSTRATE TREATMENT SYSTEM, AND COMPUTER STORAGE MEDIUM

(71) Applicant: Tokyo Electron Limited, Tokyo (JP)

(72) Inventors: Takuya Mori, Tokyo (JP); Makoto Hayakawa, Koshi (JP)

(73) Assignee: Tokyo Electron Limited, Tokyo (JP)

( * ) Notice: Subject to any disclaimer, the term of this patent is extended or adjusted under 35 U.S.C. 154(b) by 56 days.

(21) Appl. No.: 15/567,997

(22) PCT Filed: May 9, 2016

(86) PCT No.: PCT/JP2016/063733
§ 371 (c)(1),
(2) Date: Oct. 20, 2017

(87) PCT Pub. No.: WO2016/181930
PCT Pub. Date: Nov. 17, 2016

(65) Prior Publication Data
US 2018/0143144 A1 May 24, 2018

(30) Foreign Application Priority Data
May 12, 2015 (JP) .................................. 2015-097333

(51) Int. Cl.
*G01N 21/956* (2006.01)
*G01N 21/95* (2006.01)
(Continued)

(52) U.S. Cl.
CPC ....... *G01N 21/956* (2013.01); *G01N 21/9501* (2013.01); *G03F 1/84* (2013.01); *G03F 7/7065* (2013.01)

(58) Field of Classification Search
CPC .... G01N 21/956; G01N 21/9501; G03F 1/84; G03F 7/7065; G03F 1/64; G03F 1/72;
(Continued)

(56) References Cited

U.S. PATENT DOCUMENTS

2004/0151993 A1* 8/2004 Hasegawa .................. G03F 1/64
430/5
2007/0230770 A1* 10/2007 Kulkarni ............. G06F 17/5045
382/149

FOREIGN PATENT DOCUMENTS

JP 2006-147628 A 6/2006
JP 2006-242681 A 9/2006
(Continued)

OTHER PUBLICATIONS

International Search Report of the International Searching Authority dated Jul. 5, 2016 in corresponding International application No. PCT/JP2016/063733 (and English translation).

*Primary Examiner* — Jianxun Yang
(74) *Attorney, Agent, or Firm* — Posz Law Group, PLC

(57) ABSTRACT

A substrate inspection method in a substrate treatment system including a plurality of treatment apparatuses each performing a predetermined treatment on a substrate, includes: imaging a surface of a substrate before being treated in the treatment apparatuses to acquire a first substrate image; extracting a predetermined feature amount from the first substrate image; selecting an inspection recipe corresponding to the feature amount extracted from the first substrate image, from a storage unit in which a plurality of inspection recipes each set corresponding to the feature amount in a different range are stored; imaging the surface of the substrate after being treated in the treatment apparatuses to acquire a second substrate image; and determining
(Continued)

presence or absence of a defect of the substrate, based on the selected inspection recipe and the second substrate image.

8 Claims, 7 Drawing Sheets

(51) Int. Cl.
*G03F 1/84* (2012.01)
*G03F 7/20* (2006.01)

(58) Field of Classification Search
CPC ..... H01L 22/12; H01L 22/20; G06F 17/5045; G06T 7/0006
See application file for complete search history.

(56) References Cited

FOREIGN PATENT DOCUMENTS

| | | | |
|---|---|---|---|
| JP | 2007-298505 | A | 11/2007 |
| JP | 2008-002935 | A | 1/2008 |
| JP | 2012-104593 | A | 5/2012 |
| JP | 2013-205320 | A | 10/2013 |

* cited by examiner

SUBSTRATE INSPECTION METHOD, SUBSTRATE TREATMENT SYSTEM, AND COMPUTER STORAGE MEDIUM

TECHNICAL FIELD

Cross Reference to Related Application

This application is based upon and claims the benefit of priority of the prior Japanese Patent Application No. 2015-097333, filed in Japan on May 12, 2015, the entire contents of which are incorporated herein by reference.

The present invention relates to a method of inspecting a substrate, a substrate treatment system, and a computer-readable storage medium storing a program of executing the substrate inspection method.

Background Art

In a photolithography process in a manufacturing process of a semiconductor device, for example, a series of treatments such as a resist coating treatment of applying a resist solution onto a semiconductor wafer (hereinafter, referred to as a "wafer") as a substrate to form a resist film, exposure processing of exposing the resist film into a predetermined pattern, a developing treatment of developing the exposed resist film, and so on are sequentially performed to form a predetermined resist pattern on the wafer. The series of treatments are performed in a coating and developing treatment system being a substrate treatment system equipped with various treatment apparatuses which treat the wafer and transfer mechanisms which transfer the wafer and so on.

In the coating and developing treatment system, an inspection apparatus which performs so-called macro defect inspection on the wafer is provided (Patent Document 1). In the macro defect inspection, the wafer subjected to predetermined treatments in the coating and developing treatment system is imaged, for example, by an imaging apparatus such as a CCD line sensor under predetermined illumination, whereby the imaged image of the wafer is acquired. Then, the acquired imaged image is compared with a wafer image being a reference, whereby presence or absence of a defect is determined.

PRIOR ART DOCUMENT

Patent Document

[Patent Document 1] Japanese Laid-open Patent Publication No. 2012-104593

DISCLOSURE OF THE INVENTION

Problems to be Solved by the Invention

Incidentally, in the above-described macro defect inspection, the wafer image being a reference and an inspection recipe such as the illuminance of illumination and the imaging speed are set. However, various kinds of films are formed on the wafer surface in the photolithography process, so that the surface state such as reflectance and so on of the wafer surface is different in each process. This causes a problem of variation in accuracy of macro defect inspection due to the surface state of the wafer.

The present invention has been made in consideration of the point, and its object is to appropriately perform inspection of a substrate in a substrate treatment system.

Means for Solving the Problems

To achieve the above object, the present invention is a substrate inspection method in a substrate treatment system including a plurality of treatment apparatuses each performing a predetermined treatment on a substrate, the substrate inspection method including: imaging a surface of a substrate before being treated in the treatment apparatuses to acquire a first substrate image; extracting a predetermined feature amount from the first substrate image; selecting an inspection recipe corresponding to the feature amount extracted from the first substrate image, from a storage unit in which a plurality of inspection recipes each set corresponding to the feature amount in a different range are stored; imaging the surface of the substrate after being treated in the treatment apparatuses to acquire a second substrate image; and determining presence or absence of a defect of the substrate, based on the selected inspection recipe and the second substrate image.

According to the present invention, first, the substrate before being treated in the treatment station is imaged to acquire a first substrate image and the inspection recipe is selected based on the feature amount of the first substrate image, thereby making it possible to appropriately determine the presence or absence of a defect in the second substrate image, based on the optimum inspection recipe. Accordingly, it is possible to perform optimum inspection at all times without depending on the surface state of the substrate and suppress variation in accuracy of macro defect inspection.

The present invention according to another aspect is a substrate treatment system including a plurality of treatment apparatuses each performing a predetermined treatment on a substrate, the substrate treatment system including: a first imaging apparatus which images a surface of a substrate before being treated in the treatment apparatuses to acquire a first substrate image; a feature amount extraction unit which extracts a predetermined feature amount from the first substrate image; a storage unit in which a plurality of inspection recipes each set corresponding to the feature amount in a different range are stored; a recipe selection unit which selects an inspection recipe corresponding to the feature amount extracted by the feature amount extraction unit, from the inspection recipes stored in the storage unit; and an inspection apparatus including a second imaging apparatus which images the surface of the substrate after being treated in the treatment apparatuses to acquire a second substrate image, based on the selected inspection recipe, and a defect determination unit which determines presence or absence of a defect in the second substrate image.

The present invention according to still another aspect is a computer-readable storage medium storing a program running on a computer of a control unit which controls the substrate treatment system to cause the substrate treatment system to perform the substrate inspection method.

Effect of the Invention

According to the present invention, it is possible to appropriately perform substrate inspection in a substrate treatment system.

BEST MODE FOR CARRYING OUT THE INVENTION

Figure 1:
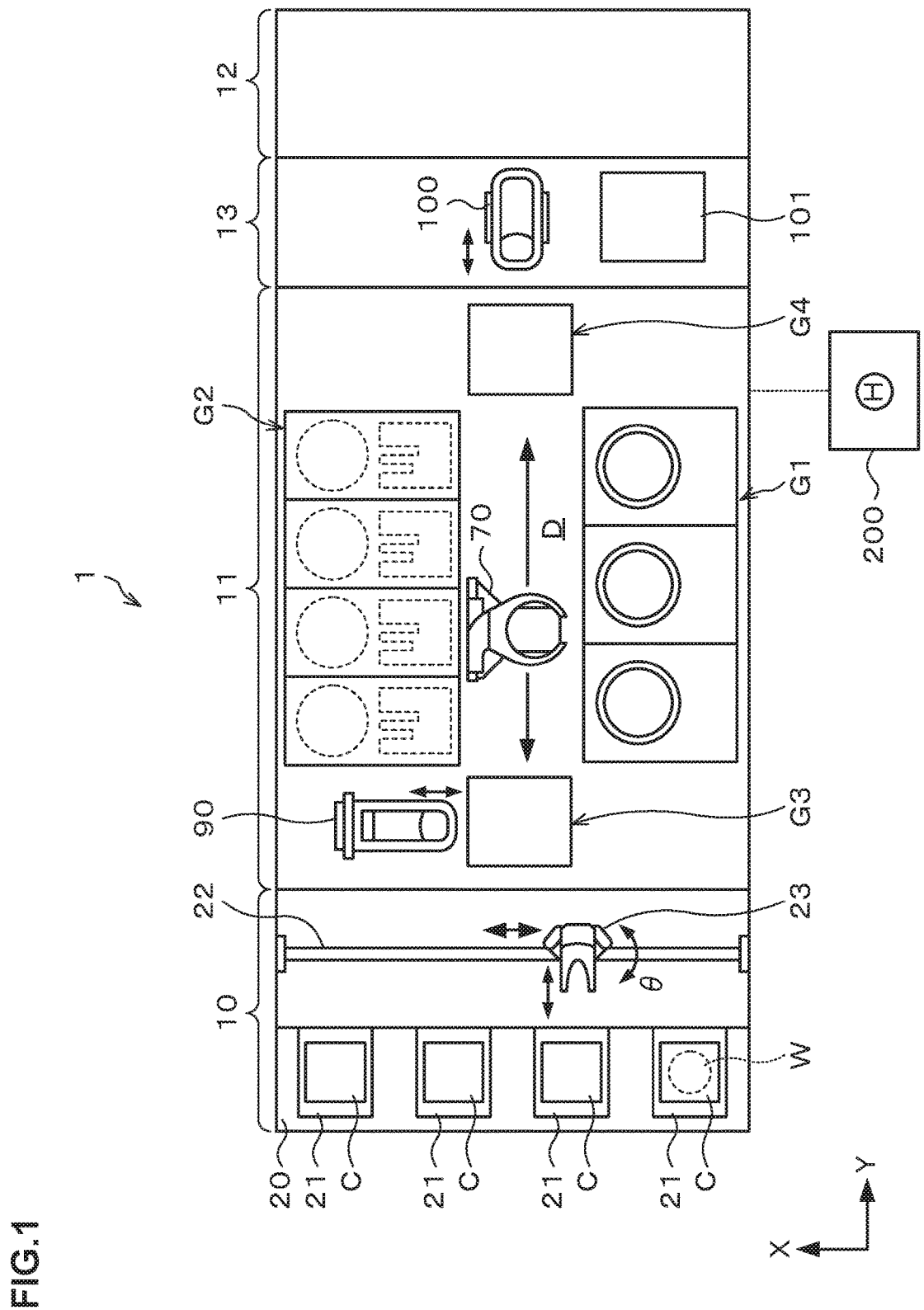
FIG. 1 A plan view illustrating the outline of a configuration of a substrate treatment system according to this embodiment.
Figure 2:
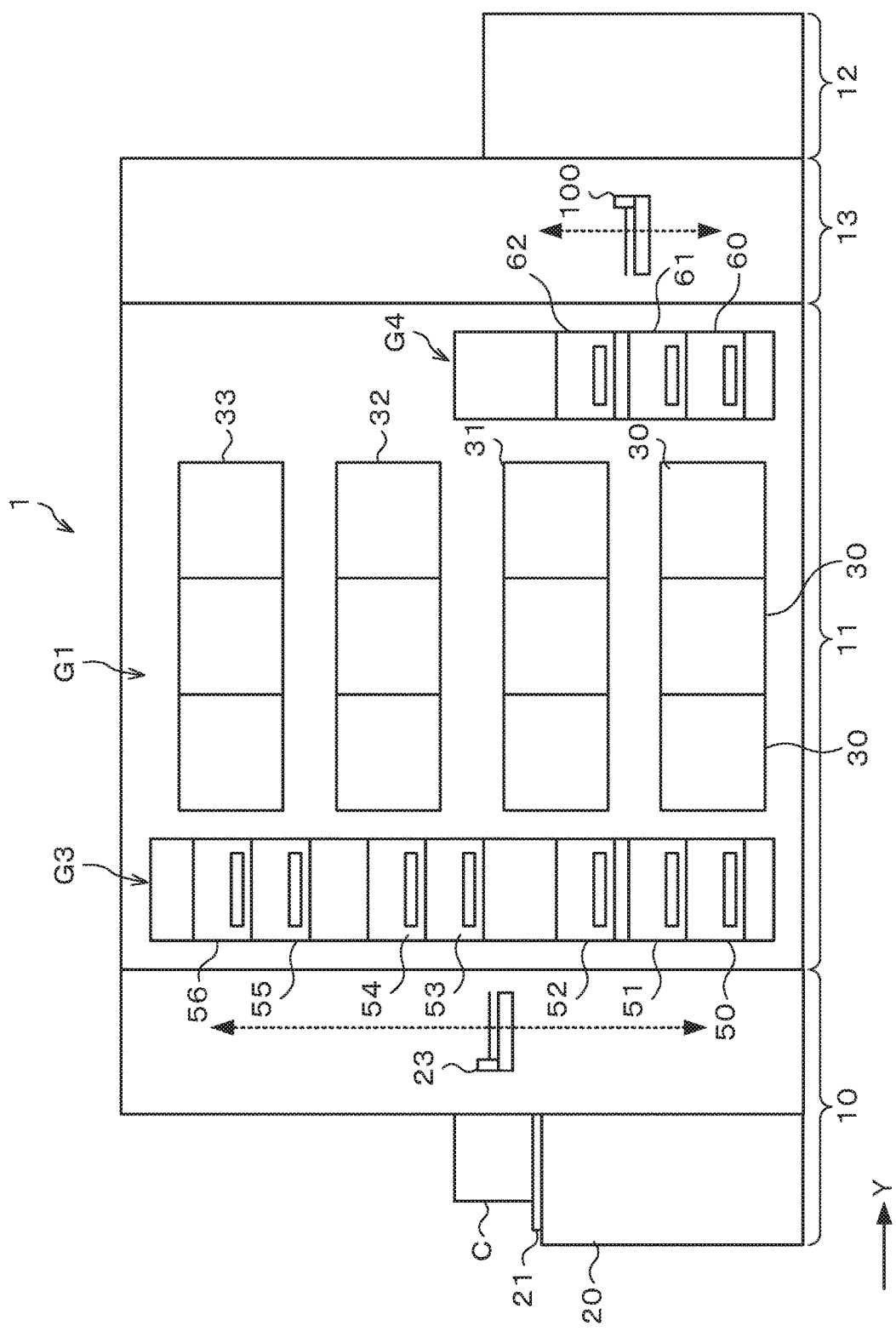
FIG. 2 A front view illustrating the outline of the configuration of the substrate treatment system according to this embodiment.
Figure 3:
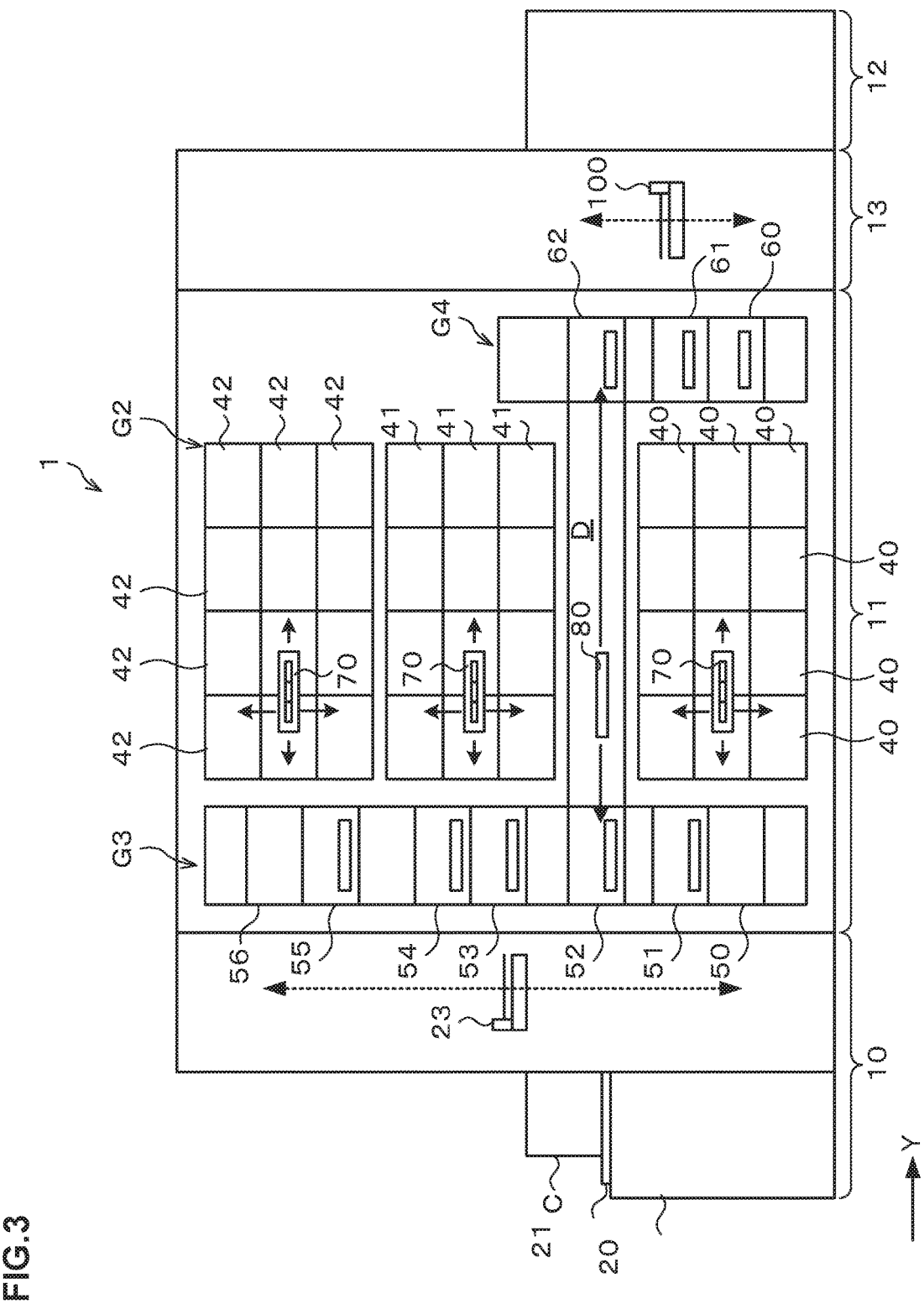
FIG. 3 A rear view illustrating the outline of the configuration of the substrate treatment system according to this embodiment.

Hereinafter, an embodiment of the present invention will be described. FIG. 1 is a plan view illustrating the outline of a configuration of a substrate treatment system 1 according to this embodiment. FIG. 2 and FIG. 3 are a front view and a rear view schematically illustrating the outline of an internal configuration of the substrate treatment system 1, respectively. Note that a case where the substrate treatment system 1 is a coating and developing treatment system for performing coating and developing treatments on the wafer W will be described as an example in this embodiment. Further, in this specification and the drawings, components having substantially the same functional configurations are denoted by the same codes to omit duplicate description.

The substrate treatment system 1 has, as illustrated in FIG. 1, a configuration in which a cassette station 10 into/out of which a cassette C housing a plurality of wafers W is transferred, a treatment station 11 which includes a plurality of various treatment apparatuses performing predetermined treatments on the wafer W, and an interface station 13 which delivers the wafer W to/from an exposure apparatus 12 adjacent to the treatment station 11, are integrally connected.

In the cassette station 10, a cassette mounting table 20 is provided. The cassette mounting table 20 is provided with a plurality of cassette mounting plates 21 on which the cassettes C are mounted when the cassettes C are transferred in/out from/to the outside of the substrate treatment system 1.

In the cassette station 10, a wafer transfer apparatus 23 is provided which is movable on a transfer path 22 extending in an X-direction as illustrated in FIG. 1. The wafer transfer apparatus 23 is movable also in a vertical direction and around a vertical axis (in a θ-direction), and can transfer the wafer W between the cassette C on each of the cassette mounting plates 21 and a later-described delivery apparatus in a third block G3 in the treatment station 11.

In the treatment station 11, a plurality of, for example, four blocks G1, G2, G3, G4 are provided each including various apparatuses. For example, the first block G1 is provided on the front side (X-direction negative direction side in FIG. 1) in the treatment station 11, and the second block G2 is provided on the rear side (X-direction positive direction side in FIG. 1) in the treatment station 11. Further, the third block G3 is provided on the cassette station 10 side (Y-direction negative direction side in FIG. 1) in the treatment station 11, and the fourth block G4 is provided on the interface station 13 side (Y-direction positive direction side in FIG. 1) in the treatment station 11.

For example, in the first block G1, as illustrated in FIG. 2, a plurality of solution treatment apparatuses, for example, developing treatment apparatuses 30 each of which performs a developing treatment on the wafer W, lower anti-reflection film forming apparatuses 31 each of which forms an anti-reflection film (hereinafter, referred to as a "lower anti-reflection film") at a lower layer of a resist film of the wafer W, resist coating apparatuses 32 each of which applies a resist solution to the wafer W to form a resist film, and upper anti-reflection film forming apparatuses 33 each of which forms an anti-reflection film (hereinafter, referred to as an "upper anti-reflection film") at an upper layer of the resist film of the wafer W, are arranged in order from the bottom.

For example, three each of the developing treatment apparatus 30, the lower anti-reflection film forming apparatus 31, the resist coating apparatus 32, and the upper anti-reflection film forming apparatus 33 are arranged side by side in the horizontal direction. Note that the numbers and the arrangement of the developing treatment apparatuses 30, the lower anti-reflection film forming apparatuses 31, the resist coating apparatuses 32, and the upper anti-reflection film forming apparatuses 33 can be arbitrarily selected.

In each of the developing treatment apparatus 30, the lower anti-reflection film forming apparatus 31, the resist coating apparatus 32, and the upper anti-reflection film forming apparatus 33, for example, spin coating of applying a predetermined coating solution onto the wafer W is performed. In the spin coating, the coating solution is discharged, for example, from a coating nozzle onto the wafer W and the wafer W is rotated to diffuse the coating solution over the front surface of the wafer W.

For example, in the second block G2, as illustrated in FIG. 3, thermal treatment apparatuses 40 each of which performs thermal treatments such as heating and cooling on the wafer W, adhesion apparatuses 41 each for enhancing adhesion between the resist solution and the wafer W, and edge exposure apparatuses 42 each of which exposes the outer peripheral portion of the wafer W, are provided side by side in the vertical direction and in the horizontal direction. The numbers and the arrangement of the thermal treatment apparatuses 40, the adhesion apparatuses 41, and the edge exposure apparatuses 42 can also be arbitrarily selected.

For example, in the third block G3, an inspection apparatus 50 that inspects the wafer W before being treated in the treatment station 11, a plurality of delivery apparatuses 50, 51, 52, 53, 54, 55, and an inspection apparatus 56 that inspects the wafer W after being treated in the treatment station 11, are provided in order from the bottom. Further, in the fourth block G4, a plurality of delivery apparatuses 60, 61, 62 are provided in order from the bottom. The configurations of the inspection apparatuses 50, 56 will be described later.

A wafer transfer region D is formed in a region surrounded by the first block G1 to the fourth block G4 as illustrated in FIG. 1. In the wafer transfer region D, for example, a plurality of wafer transfer apparatuses 70 are arranged each of which has a transfer arm movable, for example, in the Y-direction, the X-direction, the θ-direction, and the vertical direction. The wafer transfer apparatus 70 can move in the wafer transfer region D to transfer the wafer W to a predetermined apparatus in the first block G1, the second block G2, the third block G3 and the fourth block G4 therearound.

Further, in the wafer transfer region D, a shuttle transfer apparatus 80 is provided which linearly transfers the wafer W between the third block G3 and the fourth block G4.

The shuttle transfer apparatus 80 is configured to be linearly movable, for example, in the Y-direction in FIG. 3. The shuttle transfer apparatus 80 can move in the Y-direction while supporting the wafer W, and transfer the wafer W between the delivery apparatus 52 in the third block G3 and the delivery apparatus 62 in the fourth block G4.

As illustrated in FIG. 1, a wafer transfer apparatus 90 is provided adjacent on the X-direction positive direction side of the third block G3. The wafer transfer apparatus 90 has a transfer arm that is movable, for example, in the X-direction, the θ-direction, and the vertical direction. The wafer transfer apparatus 90 can move up and down while supporting the wafer W to transfer the wafer W to each of the delivery apparatuses in the third block G3.

In the interface station 13, a wafer transfer apparatus 100 and a delivery apparatus 101 are provided. The wafer transfer apparatus 100 has a transfer arm that is movable, for example, in the Y-direction, the θ-direction, and the vertical direction. The wafer transfer apparatus 100 can transfer the wafer W to/from each of the delivery apparatuses in the fourth block G4, the delivery apparatus 101 and the exposure apparatus 12, for example, while supporting the wafer W by the transfer arm.

Figure 4:
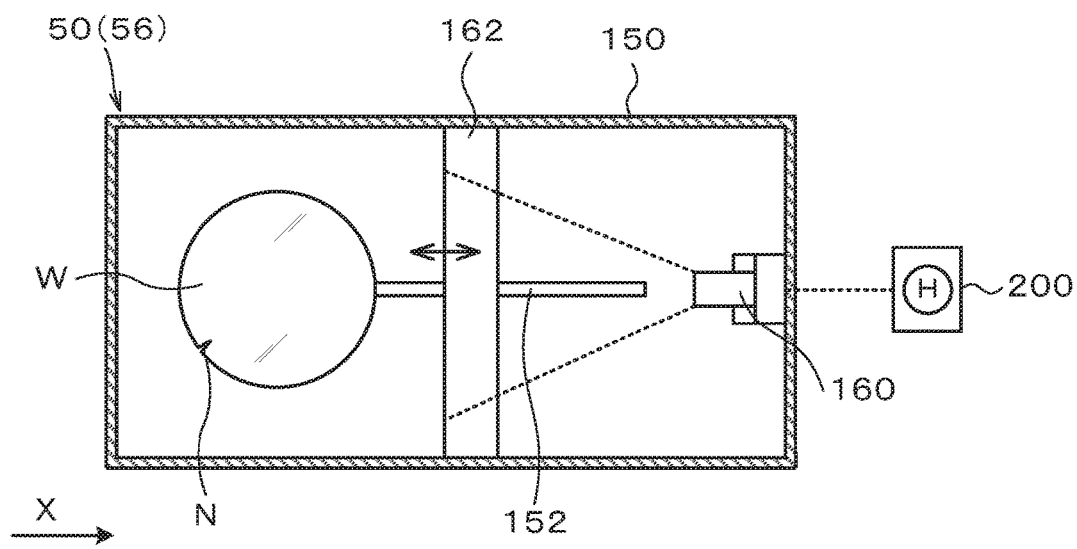
FIG. 4 A transverse sectional view illustrating the outline of a configuration of an inspection apparatus.
Figure 5:
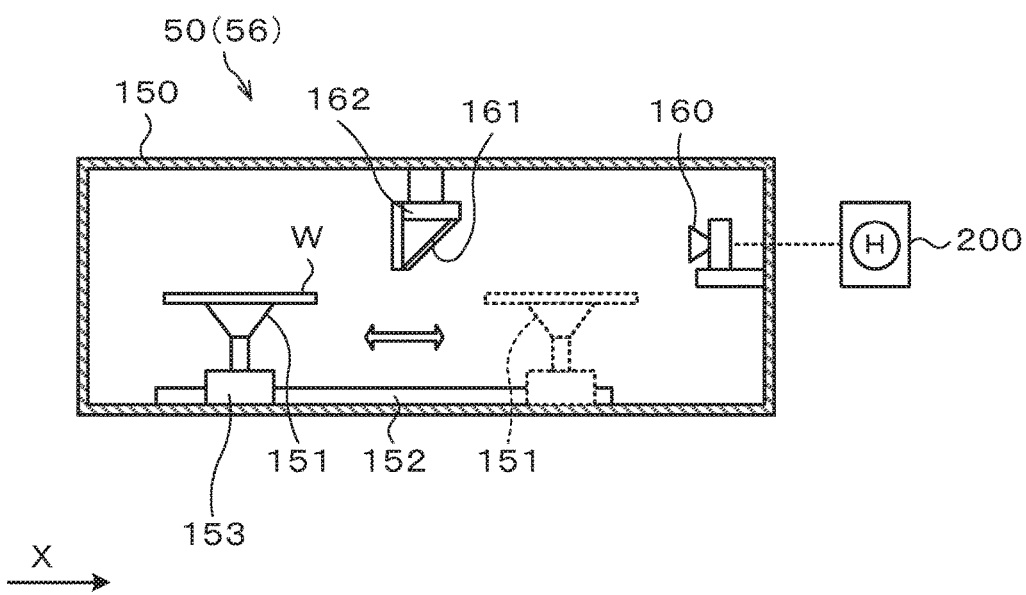
FIG. 5 A longitudinal sectional view illustrating the outline of the configuration of the inspection apparatus.

Next, a configuration of the above-described inspection apparatus 50 will be described. The inspection apparatus 50 has a casing 150 as illustrated in FIG. 4. Inside the casing 150, a wafer chuck 151 that holds the wafer W is provided as illustrated in FIG. 5. At the bottom surface of the casing 150, a guide rail 152 is provided which extends from one end side (an X-direction negative direction side in FIG. 4) to the other end side (an X-direction positive direction side in FIG. 4) in the casing 150. On the guide rail 152, a drive unit 153 is provided which rotates the wafer chuck 151 and is movable along the guide rail 152.

On a side surface on the other end side (the X-direction positive direction side in FIG. 4) inside the casing 150, an imaging unit 160 as a first imaging apparatus is provided. As the imaging unit 160, for example, a wide-angle CCD camera is used. Near the upper middle of the casing 150, a half mirror 161 is provided. The half mirror 161 is provided at a position facing the imaging unit 160 and in such a state that its mirror surface is inclined upward at 45 degrees toward the imaging unit 160 from a state of being directed vertically downward. Above the half mirror 161, an illumination device 162 is provided. The half mirror 161 and the illumination device 162 are fixed to the upper surface of the inside of the casing 150. The illumination from the illumination device 162 passes through the half mirror 161 and is applied downward. Accordingly, light reflected by an object existing below the illumination device 162 is further reflected by the half mirror 161 and captured into the imaging unit 160. In other words, the imaging unit 160 can image the object existing within an irradiation region by the illumination device 162. Then, the image of the wafer W (first substrate image) imaged by the imaging unit 160 of the inspection apparatus 50 is inputted into a later-described control apparatus 200.

Since the inspection apparatus 56 has the same configuration as that of the inspection apparatus 50, description of the inspection apparatus 56 will be omitted. Note that the imaging unit 160 of the inspection apparatus 56 functions as a second imaging apparatus of the present invention, and the image of the wafer W (second substrate image) imaged by the imaging unit 160 of the inspection apparatus 56 is similarly inputted into the control apparatus 200.

In the above substrate treatment system 1, the control apparatus 200 is provided as illustrated in FIG. 1. The control apparatus 200 is composed of, for example, a computer including a CPU, a memory and so on, and has a program storage unit (not illustrated). In the program storage unit, a program for controlling the inspection on the wafer W performed based on the substrate images imaged in the inspection apparatuses 50, 56 is stored. In addition, programs for realizing predetermined actions in the substrate treatment system 1, namely, the application of the resist solution to the wafer W, development, heat treatment, delivery of the wafer W, control of each of the units by controlling the operations of the above-described various treatment apparatuses and the drive system such as the transfer apparatuses, are also stored in the program storage unit. Note that the programs may be the ones that are recorded, for example, in a computer-readable storage medium H such as a computer-readable hard disk (HD), flexible disk (FD), compact disk (CD), magneto-optical disk (MO), or memory card, and installed from the storage medium H into the control apparatus 200.

Figure 6:
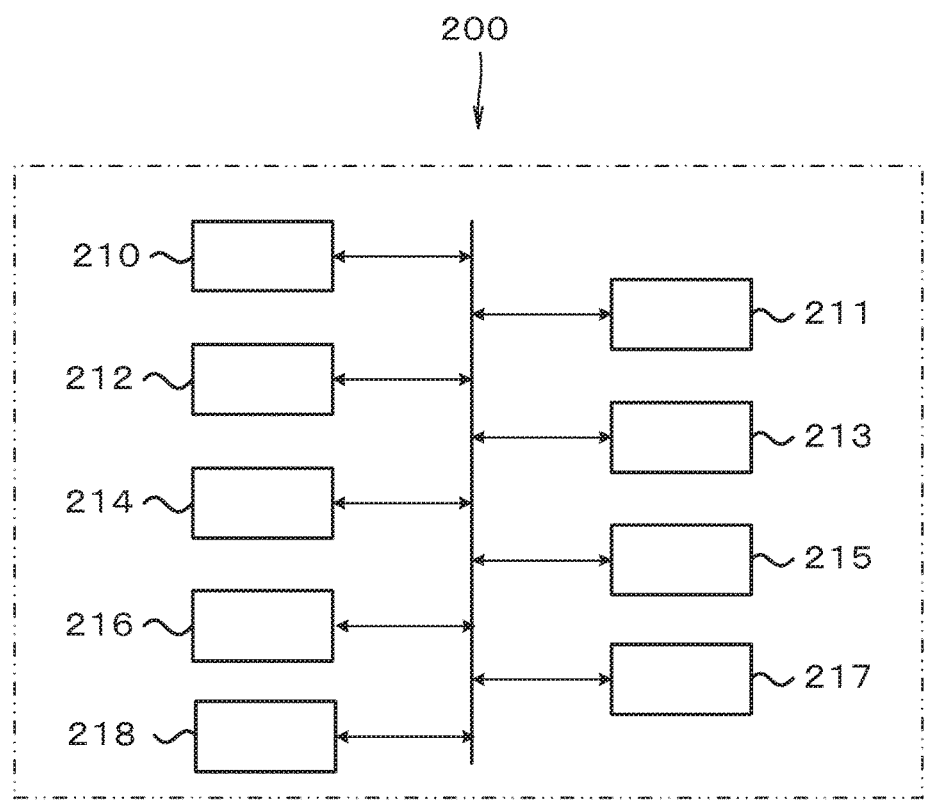
FIG. 6 A block diagram schematically illustrating the outline of a configuration of a control apparatus.

The control apparatus 200 also has, as illustrated in FIG. 6, a feature amount extraction unit 210 that extracts a predetermined feature amount from the first substrate image imaged by the imaging unit 160 of the inspection apparatus 50, a storage unit 211 in which a plurality of inspection recipes each set corresponding to the feature amount in a predetermined range are stored, a recipe selection unit 212 that selects an inspection recipe corresponding to the feature amount extracted by the feature amount extraction unit 210 from the plurality of inspection recipes stored in the storage unit 211, and a defect determination unit 213 that determines whether there is a defect or not based on the selected inspection recipe and the second substrate image imaged by the imaging unit 160 of the inspection apparatus 56. The control apparatus 200 is further provided with an image save unit 214 that saves the first substrate image and the second substrate image imaged by the imaging unit 160, an image classification unit 215 that classifies the first substrate images saved in the image save unit 214 into a plurality of groups on the basis of the feature amounts extracted by the feature amount extraction unit 210, a reference image generation unit 216 that combines the second substrate images corresponding to the plurality of first substrate images classified into each group by the image classification unit 215 to generate a reference image, and an inspection recipe generation unit 217 that generates an inspection recipe on the basis of the reference image generated by the reference image generation unit 216 and stores the inspection recipe in the storage unit 211.

The feature amount extracted by the feature amount extraction unit 210 is, for example, a pixel value of the substrate image in this embodiment. The feature amount extraction unit 210 calculates, for example, an average value of pixel values of the entire substrate image to obtain the average value as the feature amount of the substrate image. Note that a case where the substrate image is, for example, a 8-bit image of 256 gray levels (0 to 255) will be described as an example in this embodiment.

Figure 7:
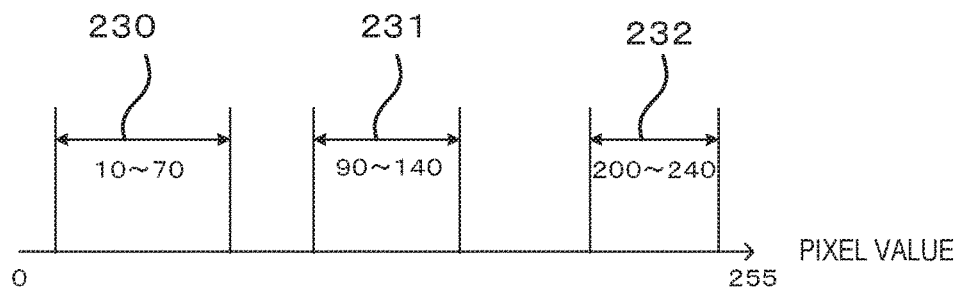
FIG. 7 An explanatory view illustrating the relation between pixel values and inspection recipes.

In the storage unit 211, for example, three kinds of inspection recipes 230, 231, 232 set according to the pixel values in different ranges are stored as illustrated in FIG. 7. The inspection recipe 230 is used, for example, when the feature amount of the first substrate image (average value of the pixel values) is within a range of "10 to 70", and the inspection recipes 231, 232 are used when the feature amounts are within "90 to 140" and "200 to 240" respectively. Each of the inspection recipes 230, 231, 232 is composed of an imaging condition when imaging is performed by each of the imaging units 160, the substrate image being the reference for defect determination and the like. Note that the number of inspection recipes stored in the storage unit 211 and the range covered by the inspection recipe can be arbitrarily set and are not limited to the contents of this embodiment.

The recipe selection unit 212 selects an inspection recipe corresponding to the feature amount extracted by the feature amount extraction unit 210 from the storage unit 211. For example, when the feature amount of the first substrate image acquired by imaging wafers W in an arbitrary lot by the inspection apparatus 50 is "60", the recipe selection unit 212 selects the inspection recipe 230 corresponding to the substrate image of the feature amount of "10 to 70" from the storage unit 211.

The defect determination unit 213 determines whether there is a defect or not based on the inspection recipe 230 and the second substrate image. Specifically, upon completion of predetermined treatments in the treatment station 11, the wafer W having the feature amount of the first substrate image of "60" is imaged by the imaging unit 160 of the inspection apparatus 56, whereby the second substrate image is acquired. The defect determination unit 213 determines whether there is a defect or not on the second substrate image of the same wafer W by the inspection recipe 230 selected based on the feature amount of the first substrate image of "60". Note that the functions of the other image save unit 214, image classification unit 215, reference image generation unit 216, and inspection recipe generation unit 217 will be described later.

Figure 8:
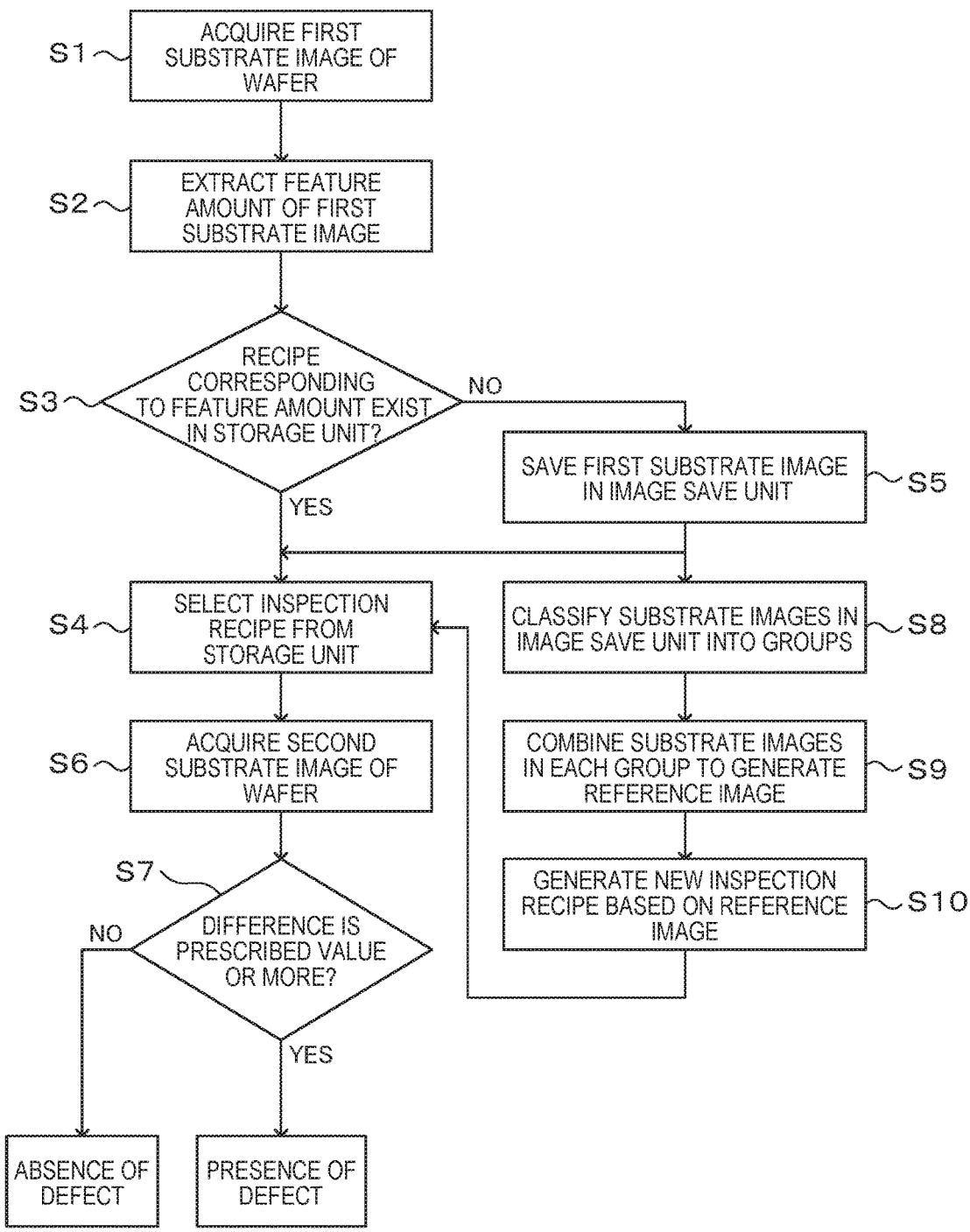
FIG. 8 A flowchart illustrating the outline of steps of inspection for a defect of a wafer.

Next, the treatment method of the wafer W and the inspection method of the wafer W performed using the substrate treatment system 1 configured as described above will be described. FIG. 8 is a flowchart illustrating an example of main steps of the inspection method of the wafer W, and the inspection method will be described based on FIG. 8.

First, a cassette C housing a plurality of wafers W in the same lot is transferred into the cassette station 10 of the substrate treatment system 1, and each of the wafers W in the cassette C is transferred by the wafer transfer apparatus 23 in sequence to the inspection apparatus 50 in the third block G3, and its first substrate image is acquired (Step S1 in FIG. 8). Then, the feature amount extraction unit 210 extracts the feature amount from the first substrate image (Step S2 in FIG. 8). Then, if an inspection recipe corresponding to the feature amount of the first substrate image exists in the storage unit 211, a predetermined inspection recipe is selected by the recipe selection unit 212 (Steps S3, S4 in FIG. 8). Specifically, when the average value of the pixel values as the feature amount is "60", the recipe selection unit 212 selects the inspection recipe 230 corresponding to the feature amount of "60" from the storage unit 211. Besides, for example, when the feature amount is "150" and a corresponding inspection recipe does not exist in the storage unit 211 (NO at Step S3 in FIG. 8), the first substrate image having a feature amount of "150" is saved in the image save unit 214 (Step S5 in FIG. 8), and a predetermined inspection recipe is selected (Step S4 in FIG. 8). The processing after the first substrate image is saved in the image save unit 214 will be described later. The predetermined inspection recipe mentioned here only needs to be, for example, an arbitrary inspection recipe of the plurality of inspection recipes stored in the storage unit 211, and explanation will be made with the inspection recipe 231 regarded as the predetermined inspection recipe in this embodiment. More specifically, when the feature amount of the first substrate image is "150", there is no corresponding inspection recipe in the storage unit 211, and therefore the predetermined inspection recipe 231 is selected.

Next, the wafer W is transferred to the thermal treatment apparatus 40 in the second block G2 and temperature-regulated. The wafer W is then transferred by the wafer transfer apparatus 70, for example, to the lower anti-reflection film forming apparatus 31 in the first block G1, in which a lower anti-reflection film is formed on the wafer W. The wafer W is then transferred to the thermal treatment apparatus 40 in the second block G2, and heat-treated and temperature-regulated.

The wafer W is then transferred to the adhesion apparatus 41 and subjected to an adhesion treatment. The wafer W is then transferred to the resist coating apparatus 32 in the first block G1, in which a resist film is formed on the wafer W.

After the resist film is formed on the wafer W, the wafer W is then transferred to the upper anti-reflection film forming apparatus 33 in the first block G1, in which an upper anti-reflection film is formed on the wafer W. The wafer W is then transferred to the thermal treatment apparatus 40 in the second block G2, and heat-treated. The wafer W is then transferred to the edge exposure apparatus 42 and subjected to edge exposure processing.

Then, the wafer W is transferred by the wafer transfer apparatus 100 to the delivery apparatus 52, and transferred by the shuttle transfer apparatus 80 to the delivery apparatus 62 in the fourth block G4. The wafer W is then transferred by the wafer transfer apparatus 110 in the interface station 13 to the exposure apparatus 12 and subjected to exposure processing into a predetermined pattern.

Then, the wafer W is transferred by the wafer transfer apparatus 70 to the thermal treatment apparatus 40 and subjected to a post-exposure bake treatment. This causes a deprotection reaction with an acid generated at an exposed portion of the resist film. The wafer W is thereafter transferred by the wafer transfer apparatus 70 to the developing treatment apparatus 30 and subjected to a developing treatment.

After the developing treatment ends, the wafer W is transferred to the thermal treatment apparatus 40 and subjected to a post-bake treatment. The wafer W is then temperature-regulated by the thermal treatment apparatus 40. The wafer W is thereafter transferred by the wafer transfer apparatus 70 to the inspection apparatus 56 in the third block G3, and the second substrate image is acquired by the imaging unit 160 (Step S6 in FIG. 8).

Then, the defect determination unit 213 of the control apparatus 200 determines whether there is a defect or not in the second substrate image, for example, on the basis of the inspection recipe 230 selected corresponding to the feature amount of "60". The determination of presence or absence of a defect is made such that the reference image in the inspection recipe 230 and the second substrate image are compared, and it is determined that there is a defect when there is a difference of a prescribed value or more between the pixel values of the reference image and the second substrate image, whereas it is determined that there is no defect when the difference is smaller than the prescribed value (Step S7 in FIG. 8). Similarly, also in the case where the feature amount of the first substrate image is "150", whether there is a defect or not is determined based on the selected inspection recipe 231 and the second substrate image.

After the defect inspection on the wafer W ends, the wafer W is transferred to the cassette C on a predetermined cassette mounting plate 21 via the wafer transfer apparatus 23, with which a series of photolithography process ends. This series of photolithography process is performed also on the subsequent wafers W in the same lot.

Next, the processing after the first substrate image is saved in the image save unit 214 at Step S5 will be described. For example, when the feature amount of "150" corresponding to none of the inspection recipes 230, 231, 232 is extracted from the first substrate image of the wafer W at the head of the lot, the feature amounts of the subsequent wafers W also become values roughly around "150". In this case, a considerable number of the first substrate images not corresponding to the inspection recipes 230, 231, 232, namely, the number of wafers W included in the lot are stored in the image save unit 214 as illustrated by broken lines in FIG. 9. Note that the vertical axis of the broken line in FIG. 9 indicates the number of substrate images saved in the storage unit 211.

Figure 9:
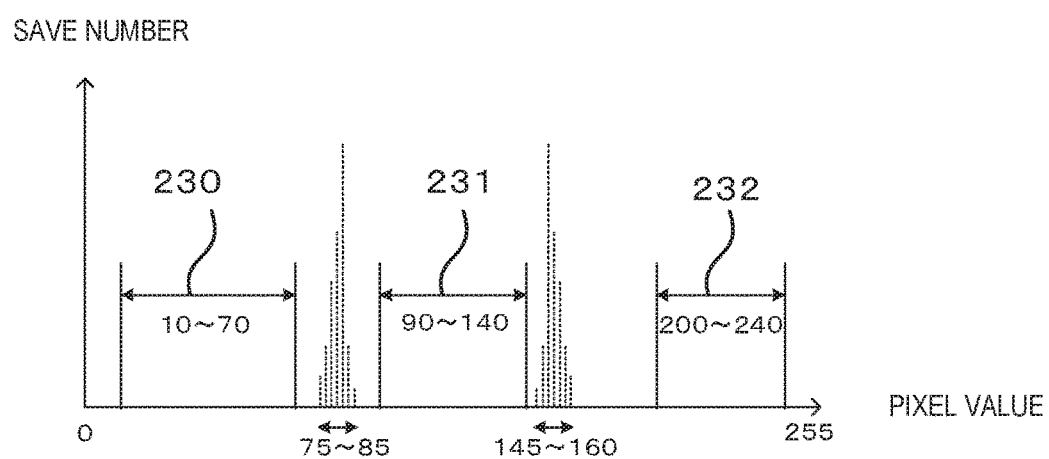
FIG. 9 An explanatory view illustrating the relation between pixel values and inspection recipes.

In the case where a considerable number of the first substrate images having pixel values, for example, in a range of 75 to 85 and a range of 145 to 160 as illustrated in FIG. 9 as a result of accumulation of the first substrate images corresponding to none of the inspection recipes 230, 231, 232 in the image save unit 214, for example, the image classification unit 215 classifies the substrate images having pixel values in the range of 75 to 85 into the first group and the substrate images having pixel values in the range of 145 to 160 into the second group (Step S8 in FIG. 8).

Then, the reference image generation unit 216 combines the second substrate images of the wafers corresponding to the first substrate images belonging to the first group to generate a reference image corresponding to this first group (Step S9 in FIG. 8). Similarly, a reference image corresponding to the second group is also generated. Subsequently, the inspection recipe generation unit 217 generates a recipe corresponding to each of the groups on the basis of the generated reference image, and the storage unit 211 stores it as a new inspection recipe (Step S10 in FIG. 8).

Then, the feature amount of the first substrate image in a subsequent lot is the one corresponding to the new inspection recipe, this new inspection recipe is selected and defect inspection is performed on wafers W at Step S4.

According to the above embodiment, first, the imaging unit 160 of the inspection apparatus 50 images the wafer W before being treated in the treatment station 11 to acquire the first substrate image, and an inspection recipe is selected based on the feature amount of the first substrate image, so that the presence or absence of a defect in the second substrate image can be appropriately determined based on an optimal inspection recipe. Accordingly, even if the surface state of the wafer W is different, for example, in each lot, an optimal inspection can be performed at all times to suppress variation in accuracy of macro defect inspection.

Besides, even when the inspection recipe corresponding to the feature amount of the first substrate image does not exist in the storage unit 211, the first substrate image is stored once in the image save unit 214 and a new inspection recipe is generated at the point in time when the first substrate image is classified into a group having a predetermined number of the first substrate images, so that the inspection recipes stored in the storage unit 211 gradually increase. Therefore, by continuing the treatments on the wafers W in the substrate treatment system 1, almost all of the first substrate images become to correspond to the inspection recipes stored in the storage unit 211, thereby enabling improvement of the accuracy of macro defect inspection.

Specifically, in the process of creating the inspection recipe, an operator needs to select a plurality of substrate images and combine the selected substrate images to create a reference image. The creation of the reference image requires lot of labor and has a problem of variations occurring in quality of the reference image depending on the level of skill of the operator. In this regard, the substrate images are classified into groups by the image classification unit 215 and a new inspection recipe is generated based on the classified substrate images, so that the inspection recipe can be appropriately generated without depending on the level of skill of the operator nor spending lot of labor.

Note that though the plurality of inspection recipes 230, 231, 232 are stored in advance in the storage unit 211 in the above embodiment, at least one inspection recipe only needs to be stored in the storage unit 211. More specifically, though inspection is performed using the one inspection recipe in the initial state of operation of the substrate treatment system 1, new inspection recipes are sequentially generated as described above to increase the inspection recipes to be stored in the storage unit 211, thereby making it possible to perform macro defect inspection corresponding to almost all of the wafers W to be transferred into the substrate treatment system 1.

Especially, the surface state of the wafer W transferred to the substrate treatment system 1 changes due to treatment recipes, for example, in other treatment apparatuses installed in a clean room including the substrate treatment system 1. Input of the surface states of the wafers W one by one into the substrate treatment system 1 leads to an increase in burden on a so-called host computer that performs batch management of the substrate treatment system 1 and the other treatment apparatuses. In this regard, the new inspection recipes are sequentially generated based on the substrate images, the wafer W before being treated in the treatment station 11 is imaged by the imaging unit 160 of the inspection apparatus 50, and its surface state is confirmed as in the present invention, thereby making it possible to perform inspection for a defect according to the surface state of the wafer W at all times without communication with the host computer.

Note that though only the first substrate image determined as "NO" at Step S3 is saved in the image save unit 214 in the above embodiment, the first substrate image determined as "YES" at Step S3 may also be saved in the image save unit 214.

Further, when all of the first substrate images are saved, the first substrate image of the wafer W at the head of the same lot of the first substrate images saved in the image save unit 214 may be employed as the reference image and a temporary inspection recipe may be generated based on this reference image by the inspection recipe generation unit 217. Further, when the wafer W at the head of the same lot is employed as the reference image and the temporary inspection recipe is generated by the inspection recipe generation unit 217, the inspection recipe does not necessarily need to be stored in advance in the storage unit 211.

Besides, though the reference image generation unit 216 combines the second substrate images to generate the reference image in the above embodiment, what kind of substrate image is used as the reference image is not limited to the contents of this embodiment. For example, a difference image generation unit 218 that generates a difference image between the first substrate image and the second substrate image may be provided in the control apparatus 200 as illustrated in FIG. 6, a plurality of the difference images may be saved in the image save unit 214, and the reference image generation unit 216 may generate the reference image on the basis of the plurality of the difference images. Then, the inspection recipe generation unit 217 generates an inspection recipe using a reference image based on the difference image.

Then, in the case of using the inspection recipe generated using the reference image based on the difference images, the difference image generation unit 218 generates the difference image of the wafer W being the object of the defect inspection, and the defect determination unit 213 determines the presence or absence of a defect of the wafer W on the basis of the generated difference image and the above-described inspection recipe generated based on the difference image. In this case, it is preferable to save also the first substrate image and the second substrate image in the image save unit 214.

Then, use of the difference image as the reference image as described above makes it possible that when the defect determination unit 213 determines that there is a defect, the defect can be determined to be caused by the substrate treatment system 1. More specifically, when a defect exists on the wafer W being the inspection object before being treated in the treatment in the treatment station 11, the defect exists both in the first substrate image and the second substrate image. Generation of the difference image between the first substrate image and the second substrate image enables removal of the defect existing before the treatments in the treatment station 11 from the difference image. Accordingly, the defect in the difference image can be determined to be caused by the treatments in the treatment station 11. Besides, when it is necessary to determine the presence or absence of defects for all of the wafers transferred out of the substrate treatment system 1 regardless of the cause of the defects, the presence or absence of a defect is confirmed, for example, for at least either their first substrate images or second substrate images saved in the image save unit 214. If a defect exists in the first substrate image or the second substrate image even when there is no defect in the difference image, the wafer W may be determined to have a defect. When a defect is detected from the first substrate image or the second substrate image, the defect can be determined not to be caused by the treatments in the treatment station 11.

Note that for generating the reference image based on the difference image in the reference image generation unit 216, it is preferable that the presence or absence of a defect is determined for the first substrate image acquired by the imaging unit 160 of the inspection apparatus 50, and the first substrate image determined to have a defect is not saved in the image save unit 214 or excluded at the time when the reference image generation unit 216 generates the reference image. When a reference image is generated by combining substrate images including defects, it may become impossible to detect a defect included in the reference image. Exclusion of the images including the defects when generating the reference image enables more accurate inspection for a defect.

Besides, for determining whether or not the defect is caused by the treatments in the treatment station 11, it is not always necessary to use the difference image but, for example, it is also adoptable to determine a defect for each of the first substrate image and the second substrate image and compare determination results. More specifically, the presence or absence of a defect of the wafer W is determined based on the second substrate image as has been described and when it is determined that there is a defect, the determination result is compared with the determination result of a defect in the first substrate image. Then, when the defect existing in the second substrate image exists also in the first substrate image, the defect can be determined to exist before the treatments in the treatment station 11. On the other hand, when the defect existing in the second substrate image does not exist in the first substrate image, the defect can be determined to be caused by the treatments in the treatment station 11. Further, in the case of determining whether the defect is caused by the treatments in the treatment station 11, it is not always necessary to save all of the first substrate images and the second substrate images themselves, but it may be adoptable to save only the determination results of the defect inspection and compare the determination results. This can reduce the burden on the control apparatus 200 for saving the images.

Note that, for example, the wafer W determined to have a defect as a result of inspection in the inspection apparatus 56 performed on the wafer W after being treated in the treatment station 11, is transferred out of the substrate treatment system 1 and then possibly subjected to correction of the defect by rework and transferred again into the substrate treatment system 1. However, when the defect is not caused by the treatments in the treatment station 11, the defect is not solved even when the rework is performed. In this case, the wafer W not contributing to production comes to be repeatedly treated in the substrate treatment system 1, resulting in a decrease in productivity. The wafer W having a defect not caused by the treatments in the treatment station 11 is prevented from being transferred again into the substrate treatment system 1, thereby avoiding such a situation.

Besides, when a defect is determined to occur due to the treatments in the treatment station 11, the transfer route in the treatment station 11 is changed, for example, for wafers W subsequent to the wafer W determined to have a defect, and determination about a defect is made for the wafers W treated in the route after change, thereby making it possible to detect a route in which the defect has occurred. In other words, in the case where a defect occurs also in the route after change, if there is a portion where the route before change and the route after change overlap, it is possible to determine that the defect occurs at the overlapping portion. Contrarily, in the case where any defect does not occur in the route after change, the overlapping portion can be determined to be not the cause of the defect.

Though the inspection apparatus 50 that inspects the wafer W before being treated in the treatment station 11 and the inspection apparatus 50 that inspects the wafer W after being treated in the treatment station 11 are used for inspecting a defect of the wafer W in the above embodiment, the specifications of the devices in the inspection apparatus 50 and the inspection apparatus 56 are preferably the same. More specifically, when the specifications of the devices in the inspection apparatus 50 and the inspection apparatus 56 are the same, it is possible to avoid a difference generated between the first substrate image and the second substrate image caused by the difference in specifications. As a result, it becomes possible to perform more accurate macro defect inspection and generate difference image.

Though the first substrate image and the second substrate image are acquired by the different inspection apparatuses 50, 56 respectively in the above embodiment, the first substrate image and the second substrate image do not always need to be acquired by different inspection apparatuses but may be acquired by the same inspection apparatus. However, the wafer W before being treated in the treatment station 11 and the wafer W after being treated are preferably imaged by separate and independent inspection apparatuses from the viewpoint of interference between transfer routes and throughput of the wafer W.

A preferred embodiment of the present invention has been described above with reference to the accompanying drawings, but the present invention is not limited to the embodiment. It should be understood that various changes and modifications are readily apparent to those skilled in the art within the scope of the spirit as set forth in claims, and those should also be covered by the technical scope of the present invention. The present invention is not limited to the embodiment but can take various forms. The present invention is also applicable to the case where the substrate is a substrate other than the wafer, such as an FPD (Flat Panel Display), a mask reticle for a photomask or the like.

EXPLANATION OF CODES 1 substrate treatment apparatus
30 developing treatment apparatus
31 lower anti-reflection film forming apparatus
32 resist coating apparatus
33 upper anti-reflection film forming apparatus
40 thermal treatment apparatus
41 adhesion apparatus
42 edge exposure apparatus
70 wafer transfer apparatus
110 treatment container
150 imaging unit
200 control apparatus
210 feature amount extraction unit
211 storage unit
212 recipe selection unit
213 defect determination unit
214 image save unit
215 image classification unit
216 reference image generation unit
217 inspection recipe generation unit
218 difference image generation unit
230, 231, 232 inspection recipe
W wafer

What is claimed:

1. A substrate inspection method in a substrate treatment system comprising a plurality of treatment apparatuses each performing a predetermined treatment on a substrate, the substrate inspection method comprising:
    imaging a surface of a substrate before being treated in the treatment apparatuses to acquire a first substrate image;
    extracting a predetermined feature amount from the first substrate image, wherein the predetermined feature amount is a pixel value of the first substrate image;
    selecting an inspection recipe corresponding to the feature amount extracted from the first substrate image, from a storage unit in which are stored a plurality of inspection recipes, each set corresponding to the feature amount in a different predetermined range of pixel values;
    imaging the surface of the substrate after being treated in the treatment apparatuses to acquire a second substrate image;
    determining presence or absence of a defect of the substrate, based on the selected inspection recipe and the second substrate image;
    saving the first substrate image and the second substrate image in an image save unit when an inspection recipe corresponding to the feature amount of the first substrate image does not exist in the storage unit;
    classifying a plurality of the first substrate images saved in the image save unit into a plurality of groups, based on the feature amounts of the first substrate images;
    combining a plurality of the second substrate images corresponding to the plurality of first substrate images classified into each of the groups to generate a reference image being a reference of defect inspection; and
    generating an inspection recipe based on the generated reference image and storing the generated inspection recipe in the storage unit,
    wherein the determination of the presence or absence of a defect of the substrate is performed based on a predetermined inspection recipe and the second substrate image.

2. The substrate inspection method according to claim 1, further comprising:
    generating a difference image between the first substrate image and the second substrate image corresponding to the first substrate image,
    wherein the determination of the presence or absence of a defect of the substrate is performed based on the selected inspection recipe and the difference image, and
    wherein the inspection recipe stored in the storage unit is for determining the presence or absence of a defect of the substrate based on the difference image.

3. A substrate inspection method in a substrate treatment system comprising a plurality of treatment apparatuses each performing a predetermined treatment on a substrate, the substrate inspection method comprising:
    imaging a surface of a substrate before being treated in the treatment apparatuses to acquire a first substrate image;
    extracting a predetermined feature amount from the first substrate image, wherein the predetermined feature amount is a pixel value of the first substrate image;
    selecting an inspection recipe corresponding to the feature amount extracted from the first substrate image, from a storage unit in which are stored a plurality of inspection recipes, each set corresponding to the feature amount in a different predetermined range of pixel values;
    imaging the surface of the substrate after being treated in the treatment apparatuses to acquire a second substrate image;
    determining presence or absence of a defect of the substrate, based on the selected inspection recipe and the second substrate image;
    generating a difference image between the first substrate image and the second substrate image corresponding to the first substrate image;
    saving the first substrate image, the second substrate image, and the difference image in an image save unit when an inspection recipe corresponding to the feature amount of the first substrate image does not exist in the storage unit;
    classifying a plurality of the first substrate images saved in the image save unit into a plurality of groups, based on the feature amounts of the first substrate images;
    combining a plurality of the difference images corresponding to the plurality of first substrate images classified into each of the groups to generate a reference image being a reference of defect inspection; and
    generating an inspection recipe based on the generated reference image and storing the generated inspection recipe in the storage unit, wherein the determination of the presence or absence of a defect of the substrate is performed based on the selected inspection recipe which is predetermined and the difference image, wherein the inspection recipe stored in the storage unit is for determining the presence or absence of a defect of the substrate based on the difference image, wherein the determination of the presence or absence of a defect of the substrate is performed based on a predetermined inspection recipe and the difference image.

4. A substrate treatment system comprising a plurality of treatment apparatuses each performing a predetermined treatment on a substrate, the substrate treatment system comprising:

a first imaging apparatus which images a surface of a substrate before being treated in the treatment apparatuses to acquire a first substrate image;

a processor configured to extract a predetermined feature amount from the first substrate image, wherein the predetermined feature amount is a pixel value of the first substrate image;

store, in a storage, a plurality of inspection recipes, each set corresponding to the feature amount in a different predetermined range of pixel values;

select an inspection recipe corresponding to the feature amount extracted by the processor, from the inspection recipes stored in the storage; and an inspection apparatus comprising a second imaging apparatus which images the surface of the substrate after being treated in the treatment apparatuses to acquire a second substrate image, based on the selected inspection recipe;

the processor is further configured to determine presence or absence of a defect in the second substrate image;

save, in an image save memory, a plurality of the first substrate image and the second substrate image;

classify the first substrate images saved in the image save memory into a plurality of groups, based on the feature amount extracted by the processor;

combine a plurality of the second substrate images corresponding to a plurality of the first substrate images classified into each of the groups to generate a reference image being a reference of defect inspection; and generate an inspection recipe based on the reference image generated by the processor and store the generated inspection recipe in the storage.

5. A substrate treatment system comprising a plurality of treatment apparatuses each performing a predetermined treatment on a substrate, the substrate treatment system comprising:

a first imaging apparatus which images a surface of a substrate before being treated in the treatment apparatuses to acquire a first substrate image;

a processor configured to extract a predetermined feature amount from the first substrate image, wherein the predetermined feature amount is a pixel value of the first substrate image;

store, in a storage, a plurality of inspection recipes, each set corresponding to the feature amount in a different predetermined range of pixel values;

select an inspection recipe corresponding to the feature amount extracted by the processor, from the inspection recipes stored in the storage; and an inspection apparatus comprising a second imaging apparatus which images the surface of the substrate after being treated in the treatment apparatuses to acquire a second substrate image, based on the selected inspection recipe;

the processor is further configured to determine presence or absence of a defect in the second substrate image;

generate a difference image between the first substrate image and the second substrate image corresponding to the first substrate image;

save, in an image save memory, the first substrate image, the second substrate image, and the difference image;

classify a plurality of the first substrate image saved in the image save memory into a plurality of groups, based on the feature amount extracted by the processor;

combine a plurality of the difference images corresponding to a plurality of the first substrate images classified into each of the groups to generate a reference image being a reference of defect inspection; and generate an inspection recipe based on the reference image generated by the processor and store the generated inspection recipe in the storage, wherein the processor is further configured to determine the presence or absence of a defect of the substrate, based on the difference image corresponding to the second substrate image.

6. A computer-readable non-transitory storage medium storing a program running on a computer of a control unit which controls a substrate treatment system to cause the substrate treatment system to perform a substrate inspection method in the substrate treatment system, the substrate treatment system comprising a plurality of treatment apparatuses each performing a predetermined treatment on a substrate, the substrate inspection method comprising:

imaging a surface of a substrate before being treated in the treatment apparatuses to acquire a first substrate image;

extracting a predetermined feature amount from the first substrate image, wherein the predetermined feature amount is a pixel value of the first substrate image;

selecting an inspection recipe corresponding to the feature amount extracted from the first substrate image, from a storage unit in which are stored a plurality of inspection recipes each set corresponding to the feature amount in a different predetermined range of pixel values;

imaging the surface of the substrate after being treated in the treatment apparatuses to acquire a second substrate image; and determining presence or absence of a defect of the substrate, based on the selected inspection recipe and the second substrate image, wherein the first substrate image and the second substrate image are saved in an image save unit when an inspection recipe corresponding to the feature amount of the first substrate image does not exist in the storage unit, wherein a plurality of the first substrate images saved in the image save unit are classified into a plurality of groups, based on the feature amounts of the first substrate images, wherein a plurality of the second substrate images corresponding to the plurality of first substrate images classified into each of the groups are combined to generate a reference image being a reference of defect inspection, wherein an inspection recipe is generated based on the generated reference image and the generated inspection recipe is stored in the storage unit, and wherein the determination of the presence or absence of a defect of the substrate is performed based on a predetermined inspection recipe and the second substrate image.

7. The computer-readable non-transitory storage medium according to claim 6, wherein a difference image between the first substrate image and the second substrate image corresponding to the first substrate image is generated, wherein the determination of the presence or absence of a defect of the substrate is performed based on the selected inspection recipe and the difference image, and wherein the inspection recipe stored in the storage unit is for determining the presence or absence of a defect of the substrate based on the difference image.

8. A computer-readable non-transitory storage medium storing a program running on a computer of a control unit which controls a substrate treatment system to cause the substrate treatment system to perform a substrate inspection method in the substrate treatment system, the substrate treatment system comprising a plurality of treatment apparatuses each performing a predetermined treatment on a substrate, the substrate inspection method comprising:

imaging a surface of a substrate before being treated in the treatment apparatuses to acquire a first substrate image;

extracting a predetermined feature amount from the first substrate image, wherein the predetermined feature amount is a pixel value of the first substrate image;

selecting an inspection recipe corresponding to the feature amount extracted from the first substrate image, from a storage unit in which are stored a plurality of inspection recipes each set corresponding to the feature amount in a different predetermined range of pixel values;

imaging the surface of the substrate after being treated in the treatment apparatuses to acquire a second substrate image; and determining presence or absence of a defect of the substrate, based on the selected inspection recipe and the second substrate image, wherein a difference image between the first substrate image and the second substrate image corresponding to the first substrate image is generated, wherein the determination of the presence or absence of a defect of the substrate is performed based on the selected inspection recipe and the difference image, wherein the inspection recipe stored in the storage unit is for determining the presence or absence of a defect of the substrate based on the difference image, wherein the first substrate image, the second substrate image, and the difference image are saved in an image save unit when an inspection recipe corresponding to the feature amount of the first substrate image does not exist in the storage unit, wherein a plurality of the first substrate images saved in the image save unit are classified into a plurality of groups, based on the feature amounts of the first substrate images, wherein a plurality of the difference images corresponding to the plurality of first substrate images classified into each of the groups are combined to generate a reference image being a reference of defect inspection, wherein an inspection recipe is generated based on the generated reference image and the generated inspection recipe is stored in the storage unit, and wherein the determination of the presence or absence of a defect of the substrate is performed based on a predetermined inspection recipe and the difference image.

* * * * *